United States Patent
Chomczynski

(10) Patent No.: US 9,827,208 B2
(45) Date of Patent: *Nov. 28, 2017

(54) ANTIOXIDANT DIETARY SUPPLEMENT COMPOSITIONS AND METHODS FOR MAINTAINING HEALTHY SKIN

(71) Applicant: Pior Chomczynski, Cincinnati, OH (US)

(72) Inventor: Pior Chomczynski, Cincinnati, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 15/421,947

(22) Filed: Feb. 1, 2017

(65) Prior Publication Data
US 2017/0157063 A1  Jun. 8, 2017

Related U.S. Application Data

(63) Continuation of application No. 11/273,514, filed on Nov. 14, 2005, now Pat. No. 9,579,298.

(60) Provisional application No. 60/632,481, filed on Dec. 2, 2004, provisional application No. 60/708,498, filed on Aug. 16, 2005.

(51) Int. Cl.
| | |
|---|---|
| A61K 36/23 | (2006.01) |
| A61K 36/81 | (2006.01) |
| A61K 36/752 | (2006.01) |
| A61K 31/01 | (2006.01) |
| A61K 45/06 | (2006.01) |
| A61K 9/00 | (2006.01) |
| A23L 33/105 | (2016.01) |

(52) U.S. Cl.
CPC ............ *A61K 31/01* (2013.01); *A23L 33/105* (2016.08); *A61K 9/0095* (2013.01); *A61K 36/81* (2013.01); *A61K 45/06* (2013.01); *A23V 2002/00* (2013.01); *A61K 2236/331* (2013.01)

(58) Field of Classification Search
CPC ....... A61K 36/23; A61K 36/81; A61K 36/752
USPC ......................................... 424/736, 766, 760
See application file for complete search history.

(56) References Cited

U.S. PATENT DOCUMENTS

| | | |
|---|---|---|
| 5,035,909 A | 7/1991 | Lomelin et al. |
| 5,871,574 A | 2/1999 | Kawaragi et al. |
| 5,962,517 A | 10/1999 | Murad |
| 6,048,846 A | 4/2000 | Cochran |
| 6,103,756 A | 8/2000 | Gorsek |
| 6,133,311 A | 10/2000 | Bok et al. |
| 6,235,721 B1 | 5/2001 | Ghosal |
| 6,605,296 B1 | 8/2003 | Stuckler |
| 6,623,769 B1 | 9/2003 | Lorant et al. |
| 6,630,158 B2 | 10/2003 | Popp et al. |
| 6,713,100 B1 | 3/2004 | Schmoutz et al. |
| 6,753,019 B1 | 6/2004 | Lang et al. |
| 6,797,303 B2 | 9/2004 | Zelkha et al. |
| 6,869,974 B1 | 3/2005 | Del Soldato |
| 7,812,057 B2 | 10/2010 | Chomczynski |
| 9,579,298 B2 | 2/2017 | Chomczynski |
| 2003/0008048 A1 | 1/2003 | Winston et al. |
| 2004/0152760 A1 | 8/2004 | Castillo et al. |
| 2004/0161435 A1 | 8/2004 | Gupta |
| 2004/0170585 A1 | 9/2004 | Berens et al. |
| 2007/0122509 A1 | 5/2007 | Chomczynski |

FOREIGN PATENT DOCUMENTS

| | | |
|---|---|---|
| CN | 1209966 A | 3/1999 |
| EP | 0 608 027 A2 | 7/1994 |
| EP | 608027 A2 * | 7/1994 |
| EP | 1 051 918 A1 | 11/2000 |
| JP | 77018218 B | 5/1977 |
| JP | H09-183914 A | 7/1997 |
| JP | 2940964 B2 | 8/1999 |
| JP | 2002-338485 A | 11/2002 |
| RU | 2039473 C1 | 7/1995 |
| WO | WO 95/16363 A1 | 6/1995 |
| WO | WO 97/47278 A1 | 12/1997 |
| WO | WO 03/041678 A1 | 5/2003 |
| WO | WO 03/079816 A1 | 10/2003 |
| WO | WO 03/105816 A1 | 12/2003 |
| WO | WO 2004/008887 A1 | 1/2004 |
| WO | WO 2006/026006 A1 | 3/2006 |
| WO | WO 2006/036125 A1 | 4/2006 |
| WO | WO 2006/046222 A2 | 5/2006 |
| WO | WO 2006/060470 A1 | 6/2006 |

OTHER PUBLICATIONS whfoods.com, Srilakshmi (2003) and Paiva et al. (1999).*
Database FSTA, International Food Information Service (Jan.-Feb. 2006) XP002478207, 1 pg.
Database WPI Week 2000347, Derwent Publications Ltd., XP002478208 (Nov. 27, 2002) pp. 1-4, 4 pgs.
Deming, D.M., et al., "Mammalian Carotenoid Absorption and Metabolism", Pure Appl Chem, 1999, 71(12):2213-2223, 11 pgs.
Economic Research Service, Market and Trade Economics Division, USDA, "Vegetables and Specialties Situation and Outlook Report", Nov. 2000, VGS-282. http://usda.mannlib.cornell.edu/reports/erssor/specialty/vgs-bb/2000/vgs282.pdf, 63 pgs.
Felter H.W., et al., "Acidum Gallicum (U.S.P.)—Gallic Acid", King's American Dispensatory, 1898, http://216.109.117.135/search/cache?p+acidum=gallicum&btn=Yahoo%21+Search&tab=W . . . , printed Jul. 8, 2005, 2 pgs.

(Continued)

*Primary Examiner* — Chris R Tate
*Assistant Examiner* — Deborah Davis
(74) *Attorney, Agent, or Firm* — Frost Brown Todd LLC

(57) ABSTRACT

Compositions and methods for maintaining healthy skin and alleviating skin conditions such as redness, inflammation, irritation and skin aging, as well as for maintaining healthy scalp and hair are disclosed. The oral compositions disclosed comprise antioxidants including lycopene, gallic acid and ascorbic acid. Preferably lycopene has been water-extracted, more preferably under acid conditions. In the method of treatment aspect of the invention, an oral composition containing antioxidant(s) is administered to a person concurrently with a topical treatment for said skin conditions. Preferred topical compositions comprise cyclohexane polyols, such as cyclohexanediol or cyclohexanetriol.

5 Claims, No Drawings

(56) References Cited

OTHER PUBLICATIONS

Friedman, M., et al., "Effect of pH on the Stability of Plant Phenolic Compounds", J Agri Chem, 2000, 48:2101-2110, 11 pgs.
Giovanelli, G., et al. "Stability of Dried and Intermediate Moisture Tomato Pulp During Storage", Journal of Agricultural and Food Chemistry, 2002, 50:7277-7281, 5 pgs.
H.J. Heinz Company, sponsor, "Lycopene", www.lycopene.org, printed Feb. 6, 2006, 2 pgs.
Hayes, WA. et al., "The Production and Quality of Tomato Concentrates", Critical Reviews in Food Science and Nutrition, 38(7):537-564, 1998, 29 pgs.
Heflebower, R., et al., "The Influence of Different Tomato Varieties on Acidity as It Relates to Home Canning", *Journal of Extension*, 48/6, Dec. 2010, 5 pgs.
Hermann, K., "Lexikon Lebensmittel and Ernahrung," Ceres-Verlag Rudolf-Aigst Petler LG (1989), p. 110, 3 pgs.
Hof, K.H., et al., "Carotenoid Bioavailability in Humans from Tomatoes Processed in Different Ways Determined from the Carotenoid Response in the Triglyceride-Rich Lipoprotein Fraction of Plasma after Single Consumption and in Plasma after Four Days of Consumption", J. Nutr, 2000, 130:1189-1196, 8 pgs.
Institute of Naturaopathy Staff. *Nutrition and Health: The Vegetarian Way*. Sterling Publishers Pvt Ltd, 2002, p. 39, 1 pg.
Khachik, F., et al., "Chemistry, Distribution, and Metabolism of Tomato Carotenoids and Their Impact on Human Health", Exp Biol Med, 2002, 227:845-851, 7 pgs.
Lee et al., "Cocoa Has More Phenolic Phytochemicals and a higher Antioxidant Capacity than Teas and Red Wine", J. Agric. Food Chem., 2003, 51(25):7292-7295, 9 pgs.
Lycopene. Retrieved from the internet. <http://en.wikipedia.org/wiki/Lycopene>. Retrieved on Dec. 3, 2009, 7 pgs.
Mahoney, L. "Lighten Up, Ignite a Passion for Healthful Food from the Grill," Richmond Times, Jun. 26, 2002, pp. 1-4, 4 pgs.
Mango. Retrieved from the internet http://en.wikipedia.org/wiki/Mango, Retrieved on Jun. 23, 2008, 11 pgs.
McClude, S. *Preserving Summer's Bounty: A Quick and Easy Guide to Freezing, Canning, Preserving and Drying What You Grow*. Rodale. 1998. p. 65, 1 pg.
Meyerowitz, S. *Juice Fasting and Detoxification: Use the Healing Power of Fresh Juice to Feel Young and Look Great*. Sproutman Publications, 1999, pp. 32-33, 2 pgs.
National Rosacea Society, "14 Million Americans Have Rosacea and Most of Them Don't Know It," www.rosacea.orq, printed Aug. 4, 2005, 1 pg.
O'Neil, M., et al., eds., "Propyl Gallate," The Merck Index, 13th Edition, 2001, p. 1406, Merck & Co., Inc., Whitehouse Station, NJ, USA, 2 pgs.
Ow, Y.Y., et al., "Gallic Acid and Gallic Acid Derivatives: Effect on Drug Metabolizing Enzymes", Curr. Drug Metab., Jun. 2003, 4(3):241-248, 2 pgs.
Paiva, S., MD, et al., "Beta-Carotene and Other Carotenoids as Antioxidants," J Am Coll Nutr. Oct. 1999; 18 (5); 426-433, 8 pgs.
Pollack, S., "Characteristics of U.S. Orange Consumption," Outlook Report No. FTS30501, Economic Research Service, USDA, Aug. 2003, www.ers.usda.gov/publications/fts/aug03/fts30501/, 1 pg.
Schwartz, R., "Too Much Meat, Too Few Veggies May Cause Prostate Cancer", The Ottawa Citizen, Apr. 24, 1996, pp. 1-3, 3 pgs.
Shahrzad S., et al., "Pharmacokinetics of Gallic Acid and Its Relative Bioavailability from Tea in Healthy Humans", J. Nutr., 2001, 131:1207-1210, 10 pgs.
Soya. Retrieved from the internet <http://www.soya.be/soybean-oil.php>. Retrieved on Jul. 20, 2009, 1 pg.
Srilakshmi, B., *Food Science*. New Age International. 2003. p. 177, 1 pg.
The World's Healthiest Foods. <http://www.whfoods.com/genpage.php?tname=george&dbid=63>. Retrieved on Jul. 20, 2009. pp. 1-3, 3 pgs.
Tombak, M. *Can We Live 150 Years?: your body maintenance handbook*. New Wave Internet Services, 2003, p. 89, 1 pg.
Tyssandier, V., et al., "Processing of Vegetable-Borne Carotenoids in the Human Stomach and Duodenum", A. J. Physiol Gastroinest Liver Physiol, 2003, 284:G913-G923, 13 pgs.
Canadian Office Action dated Apr. 25, 2014 for Application No. CA 2,856,865, 4 pgs.
International Search Report dated May 9, 2006 for Application No. PCT/US2005/043301, 4 pgs.
International Preliminary Report on Patentability and Written Opinion dated Jun. 5, 2007 for Application No. PCT/US2005/043301, 9 pgs.
International Search Report dated Jun. 30, 2008 for Application No. PCT/US2007/083696, 5 pgs.
International Preliminary Report on Patentability and Written Opinion dated May 19, 2009 for Application No. PCT/US2007/083696, 8 pgs.
U.S. Appl. No. 60/632,481, filed Dec. 2, 2004.
U.S. Appl. No. 60/708,498, filed Aug. 16, 2005.

* cited by examiner

ANTIOXIDANT DIETARY SUPPLEMENT COMPOSITIONS AND METHODS FOR MAINTAINING HEALTHY SKIN

CROSS-REFERENCE TO RELATED APPLICATIONS

This application is a continuation of U.S. patent application Ser. No. 11/273,514, Chomczynski, filed Nov. 14, 2005, granted as U.S. Pat. No. 9,579,298 and is related to and claims priority from U.S. Provisional Application Ser. No. 60/632,481, Chomczynski, filed Dec. 2, 2004, and U.S. Provisional Application Ser. No. 60/708,498, Chomczynski, filed Aug. 16, 2005, all of which are incorporated herein by reference.

TECHNICAL FIELD

The present invention relates to the use of antioxidant dietary supplements, alone and together with topical treatments, for maintaining healthy skin and alleviating skin conditions such as redness, inflammation, irritation and skin aging.

BACKGROUND OF THE INVENTION

A proper diet is a contributing factor in maintaining healthy skin. There are a variety of known dietary supplements which can affect human skin conditions. (International Cosmetic Ingredient Dictionary and Handbook, 2004; and U.S. Pharmacopoeia Dietary Supplement Monographs).

In my previous patent application (Chomczynski, U.S. patent application Ser. No. 10/925,851, filed Aug. 25, 2004) we disclosed that oral administration of tomato products can be beneficial for maintaining healthy skin and for treatment of skin conditions, when used in conjunction with a topical treatment including cyclohexanol derivatives. It was disclosed further that an active component(s) of tomato is associated with a water insoluble tomato residue. The water insoluble tomato residue is mainly composed of plant polysaccharides forming a matrix inter-spaced with water insoluble tomato components, most notably carotenoids. There are several carotenoids which have been identified (Khachik et al., 2002) in tomato (*lycopersicum esculantum* and its wild variety). The most characteristic carotenoid found in tomato is lycopene. Lycopene is present in high concentration in ripe tomato fruits and also in watermelons, pink grapefruits, pink guavas and papayas.

Known beneficial health effects of lycopene include: reducing risk of cancer (such as prostate cancer), and protecting tissues from oxidative damage especially protecting proper function of the human eye (Khachik et al. 2002). Lycopene has been used in cosmetic compositions and oral supplements in humans (www.lycopene.org).

Lycopene has also been used as a part of cosmetic and medical compositions to improve skin health. In cosmetic compositions, Berens et al. (U.S. Published Patent Application 2004/0170585, published Sep. 2, 2004, par. 19) used lycopene as an antioxidant in the treatment of skin pigment disorders. Cochran describes compositions for providing nutrients and regulatory components to the human body; those compositions include lycopene as an antioxidant (U.S. Pat. No. 6,048,846, Cochran, issued Apr. 11, 2000).

Gupta, in U.S. Published Patent Application 2004/0161435, published Aug. 19, 2004, discloses topical treatment of skin aging promoting collagen and elastin in the skin by a treatment with a composition including lycopene.

Lycopene is included in topical compositions to treat human skin to affect tanning activity (WO 97/47278) and for treatment of the scalp and/or acne affecting 5 alpha-reductase activity (JP-2940964).

Popp et al, describes a dietary supplement composition for promoting healthy skin with lycopene as a part of composition containing other necessary ingredients such as vitamins, microelements and other chemically defined components (U.S. Pat. No. 6,630,158, issued Oct. 7, 2003). The supplement is provided in the form of a tablet, powder, capsule, wafer, liquid or liquid filled capsule.

Gorsek describes treatment of age-related eye ailments with an orally ingested composition including lycopene (U.S. Pat. No. 6,103,756, issued Aug. 15, 2000).

Lorant et al. (U.S. Pat. No. 6,623,769, issued Sep. 23, 2003) uses lycopene in the form of a suspension or solution for oral administration and for topical application to improve cutaneous skin aging.

Adsorption by humans of lycopene from dietary sources can be as low as 2,5% (Tyssandier et al., 2003), Heating and processing tomatoes into tomato paste increases bioavailability of lycopene (Hof, 2000), Also, presence of oil increases bioavailability of lycopene (Deming, 1999, p. 2216), Plant fiber can be used as a dietary supplement to obtain a beneficial effect on bowel health (U.S. Pat. No. 6,753,019, Lang et al., issued Jun. 22, 2004), The fiber described in the '019 patent includes water-extracted tomato fiber. The extracting fluid is most preferably water, but organic solvents such as chloroform and hexane can also be used for the extraction (p. 6). Since lycopene is soluble in both chloroform and hexane, the benefit of the fiber composition described in the '019 patent does not appear to be related to lycopene. In addition, it is indicated that the extracted material was not treated with either acid or alkali (claim 14).

Schmoutz et al (U.S. Pat. No. 6,713,100, issued Mar. 30, 2004) describes confectionary products comprising at least 25% fat, 6% to 15% sugar, and at least 15% vegetable solids, The vegetable solids can include tomato solids (claim 6).

In addition to lycopene, various antioxidants were used as an adjunct part of dietary supplement to improve skin conditions (International Cosmetic Ingredient Dictionary and Handbook, 2004; and U.S. Pharmacopoeia Dietary Supplement Monographs, Vaya 2, 1).

U.S. Pat. No. 5,962,517 (Murad, issued Oct. 5, 1999) describes pharmaceutical compositions and methods for treating acne based on the use of zinc and vitamin A. These compositions comprise, as an adjunct ingredient, vitamin C, and can be administered topically or orally.

U.S. Pat. No. 6,235,721 (Ghosal, issued May 22, 2001) describes a stabilized antioxidant formulation comprising vitamin C supplemented with 0-5% gallic acid. The role of gallic acid in the invention is to stabilize and prevent oxidation of vitamin C.

U.S. Pat. No. 6,869,974 B1 (Del Soldato, issued Mar. 22, 2005) describes the use of certain pharmaceutical compounds to address the oxidative stress in pathological situations, including acne. The described compounds are synthetic multi-component molecules with precursor subcomponents comprising gallate and ascorbate moieties.

Gallic acid (trihydroxy benzoic acid), a potent antioxidant, is described as an anti-mutagenic, anti-carcinogenic and anti-inflammatory agent (Shahrzad, 2001). High concentration of gallic acid, either as single molecule or as a building block of polyphenols, are found in tea, wine (Singleton, Adv Dietary Res, 1981, 27, 149-242) and cocoa (Lee, 2003).

In addition, U.S. Published Patent Application 2004/0152760 A1 (Castillo et al., published Aug. 5, 2004) describes the use of polyhydroxylated compounds and compositions for the treatment of amyloidosis, especially Alzheimer's disease. The useful compounds comprise gallic acid and its derivatives. The useful compositions also include ascorbic acid as an antioxidant.

SUMMARY OF THE INVENTION

The present invention relates to orally administered compositions used to alleviate symptoms of skin conditions, including redness, break-outs and flare-ups often associated with acne, rosacea and inflammation. The compositions comprise antioxidants including lycopene, gallic acid and ascorbic acid.

The present invention also relates to a method of maintaining healthy skin and relieving skin conditions associated with inflammation, irritation and skin aging, comprising administering to a subject in need of such treatment a topical skin treatment at the site of said skin condition, together with the oral administration to said subject of an antioxidant composition comprising lycopene, gallic acid and/or ascorbic acid. The preferred compositions for administration of lycopene are compositions which have been water extracted, preferably under acidic conditions. The preferred administration of other antioxidants are compositions containing substantially purified antioxidant(s) administered as an oral pill.

The preferred topical compositions are based on the active compound

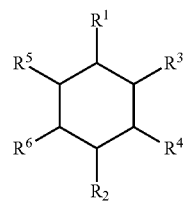

wherein $R^1$ is selected from —OH, and $C_1$-$C_3$ alkyl OH; and $R^2$, $R^3$, $R^4$, $R^5$ and $R^6$ are each independently selected from —H, —OH, COOH, $C_1$-$C_6$ alkyl and $C_3$-$C_6$ cycloalkyl; provided that the active includes no more than five —OH groups.

All patents, published patent applications, and publications discussed in this application are incorporated by reference herein.

DETAILED DESCRIPTION OF THE INVENTION

The present invention relates to antioxidant dietary supplement compositions and methods for maintaining healthy skin, and for alleviating a number of skin conditions, including skin redness and inflammation, which are associated with skin ailments such as inflammation, irritation and skin aging. Examples of skin ailments benefiting from the present invention include acne and rosacea.

The approach of the present invention is to combine oral administration of medically active supplements comprising lycopene and/or other antioxidants with topical treatments to obtain the benefit of skin health and to treat symptoms of skin ailments.

The antioxidant supplement in the current invention can further comprise synthetic and/or natural compounds or materials, known as dietary supplements, or mixtures of these compounds and materials. Examples of these compounds and materials are listed in the International Cosmetic Ingredient Dictionary and Handbook 2004, and in the U.S. Pharmacopeia Dietary Supplement Monographs, and include, for example, vitamins, microelements, natural extracts, hormones, proteins, carbohydrates, and combinations thereof.

Lycopene can be utilized in the present invention as a purified compound or as a component of a plant-derived material. The purified lycopene can be used in the present invention as a solution in hydrophobic liquids, in the form of pills or as a dispersion in solid or fluid materials. The effective amount of lycopene administered in the treatment regimen of the present invention is from about 0.2 mg/kg to about 3 mg/kg of body weight. The preferred amount is from about 0.3 mg/kg to about 1.0 mg/kg of body weight. The lycopene supplement may also comprise natural or synthetic components modifying or enhancing its taste and/or color. The lycopene supplement may also include other antioxidants and components enriching and modifying its dietary value including, for example, protein and carbohydrate additives or a variety of dietary components required by a diet regimen.

The plant-derived material containing lycopene might be in the form of juice, extracts, suspensions and solids. The source of plant materials containing lycopene may include, but is not limited to, tomato, pink grapefruit, rosehip, pink guava and papaya. The lycopene-containing material can be supplemented with other, antioxidants either in substantially pure form or as components of plant-derived material. Currently, the common additive to tomato juice is ascorbic acid. The preferred antioxidants additives in the current invention comprise hydroxylated phenols, flavonoids and polyphenols. The preferred compositions comprise tomato juice supplemented with gallic acid, flavonoids or cocoa, or a mixture of these supplements.

The preferred form of lycopene in the supplements of the present invention is dispersion in a solid matrix. The solid matrix can be a plant solid containing dispersed lycopene. Examples of a lycopene dispersion in plant solids include juice-containing solids, sauce and paste concentrate. These materials may be derived from any plant either naturally containing lycopene or from a lycopene dispersion made in vitro. The preferred plant solid is tomato solid containing lycopene. The lycopene supplement can also be in the form of a pill or a capsule, utilizing conventional pharmaceutical carriers and manufacturing techniques.

It has now been discovered that water-extracted plant solids are preferred over the non-extracted plant solids. Unexpectedly, water extraction increases potency of plant solids in their beneficial effects on health and skin. It has further been discovered in the current invention that the most effective water-extracted plant solids are solids extracted with water at acidic pH. The acidic extraction should be performed at pH below about 6, and preferably at a pH range from about pH 1.5 to about pH 4. The pH of the solution can, for example, be adjusted with HCl. The preferred extraction conditions are ambient temperature (range about 15° C.-25° C.) and atmospheric pressure. The extraction typically takes from about 1 hour to about 12 hours. There can be a single round or multiple rounds of water and/or acidic water extraction.

It has also been discovered in the present invention that an important component of the water-extracted plant solids is lycopene and that acid-extracted plant solids are the most effective formulation providing lycopene. Purified lycopene administered in pills is less effective. Dispersion of lycopene in a plant matrix contributes to lycopene's effectiveness in the methods of treatment of the present invention. In addition to lycopene, the water-extracted plant solids retain several compounds contributing to health and/or skin health, for example, polysaccharides, glycoalkaloids and carotenoids, Carotenoids, with their antioxidative activity, especially contribute to lycopene effectiveness in the methods of treatment of the present invention. These beneficial carotenoids include compounds such as phytoene, phytofluene, carotens, neurosporene and lutein.

The lycopene-containing plant solids of this invention can be administered as a dietary supplement in the form of paste, powder or suspension. They can be administered as a part of oral/topical administration of the present invention or as stand alone dietary products. The lycopene solid supplement may also contain components originating from more than one plant source. It may also comprise non-lycopene-containing plant solids and other plant-derived components, such as juice, extracts, powders and puree.

The water-extracted tomato paste or acidic-water extracted tomato paste loses most of its tomato taste and odor as compared with the unextracted paste. The organoleptic characteristics of tomato can be further modified by mixing the extracted tomato product with other components, such as juice, extracts or puree, derived from a variety of sources including apple, banana, pear, grapes, cocoa and herbs.

The taste changing additives allow for substitution of salt in tomato products.

The lycopene solid supplement may also comprise chemical (synthetic or natural) components changing or enhancing its taste, odor and color. The lycopene supplement may further comprise components enriching and modifying its dietary value including, for example, protein, carbohydrate and other dietary additives as required by a diet. A diet may include consumption of the lycopene-containing product alone or concurrently with the topical treatment of current invention.

The lycopene solid supplement may also include components increasing the bioavailability of the lycopene. Said components include hydrophobic liquids, such as sesame oil, corn oil, olive oil or canola oil. The choice of products with various organoleptic and dietary properties is beneficial for the treatment disclosed in the present invention.

The lycopene solid supplement may further comprise components with a beneficial effect on health and/or skin including, for example, added antioxidants, vitamins and microelements. The preferred added antioxidant is gallic acid. To improve the organoleptic and health characteristics of the extracted or un-extracted tomato products they can be mixed with cocoa. In addition to the improved taste, this dietary composition is naturally enriched in gallic acid and other cocoa antioxidants and constituents (Ki, 2003).

Currently, tomato and other fruit juices are fortified with vitamin C to improve stability and health benefits of the juice product. It is disclosed in the current invention that gallic acid can be added to fruit and vegetable juices, purees and other food products as an antioxidant to substitute for vitamin C, or can be added together with vitamin C. In addition to its higher antioxidant potency, gallic acid is more effective than vitamin C in suppressing skin ailments including the symptoms observed in acne and rosacea. To form a stable product with gallic acid as an additive in un-oxidized form, a fruit or vegetable juice and other food product should have acidity about pH 5 or lower. This stability of gallic acid is unexpected since Friedman et al., 2000, found that gallic acid was unstable and it was not recommend as a food preservative. Friedman, however, did not test stability of gallic acid in solutions with acid pH.

In the current invention, gallic acid can be added to an un-extracted or extracted tomato juice of other food products comprising juices, purees and dry foodstuff. For example, pineapple, grape juices apply puree can be supplemented with gallic acid. Preferably, gallic acid can be supplemented in the range of about 10 mg to about 2 g per liter, and more preferably in the range of from about 0.3 g to about 1 g per liter. In addition to beneficial effects on the skin, compositions of the current invention can be used as a source of antioxidants in health and sport drinks and other foodstuff. Another preferred way of preparing gallic acid and other antioxidants for use in this invention is preparation of a solid supplement, preferably in the form of an oral pill. The solid supplement secures long-term shelf life of antioxidants. Esters of gallic acid including propyl gallate were used in cosmetics and food industry as antioxidant additives (Merck Index, 2004). However, esters of gallic acid are not active in improving skin conditions in the current invention.

As indicated in the Background section, lycopene and other antioxidants have been used as a part of compositions and methods to improve skin conditions. Additional examples include:

Hedgpeth et al., in U.S. Published Patent Application 2004/0223932 A1, published Nov. 11, 2005, describes the adhesive treatment for acne which includes topical application of gallic acid as an anti-acne compound.

McDaniel in U.S. Pat. No. 6,887,260 B1, issued May 3, 2005, describes a method and apparatus involving the use of UV light for acne treatment which comprise a topical application of vitamin C and other antioxidants, Marion et al, in U.S. Published Patent Application 2005/0004146 A1, published Jan. 6, 2005, described compositions and methods for skin redness treatment employing caffeine and comprising various adjunct compounds including antioxidants.

In the current invention it has been found that an antioxidant alone when administered concurrently with a topical treatment is sufficient to evoke beneficial effects on skin. The administration of purified or partially purified antioxidants allows elimination of the dietary supplements compounds which negatively affect skin conditions. For example, tea, coffee, chocolate and spices are known to contain various antioxidants and other ingredients beneficial for human health (Ki et al., 2003). However, rosacea sufferers should avoid drinking tea, coffee and certain spices since they induce skin inflammatory responses such as redness, breakouts and flare-ups (National Rosacea Society website www.rosacea.org). It is unknown what particular ingredients in the foodstuff are responsible for inducing skin inflammatory responses.

The preferred compositions of antioxidants in the current invention comprise substantially pure antioxidant or a mixture of substantially pure antioxidants. The unpurified or partially purified plant extracts or other plant-derived material containing antioxidants can also be used in the current invention. The most preferred antioxidants for use in the present invention are gallic acid, ascorbic acid and their active derivatives, and mixtures thereof. Gallic acid esters such as methyl gallate and propyl gallate are not effective in oral compositions of the current invention. Examples of other antioxidants which can be used in the current invention comprise rutin, hydroxytyrosol, caffeic acid and oleuropein.

Gallic acid is a compound present in a variety of plants, most notably in tea, grapes and cocoa. As a component of plant extracts or in purified form gallic acid was used in traditional remedies (Felter, 1898). Currently, gallic acid and its esters have a diverse use due to their anti-cancer and anti-microbial properties (Ow, 2003). Gallic acid and its esters can supplement topical compositions of the present invention as adjunct antimicrobial agents.

The oral antioxidant combined with topical treatment of the current invention is especially effective for improving skin redness and inflammatory conditions in acne and rosacea. Both skin diseases are known to be affected by a multitude of factors including bacterial, fungi, hormonal and immunological factors. It is disclosed in the current invention that unexpectedly skin conditions arising from acne and rosacea can be improved by the addition of a supplement containing only an antioxidant or mix of antioxidants.

The antioxidant amount in the human diet can be related to the amount of vitamin C. Currently, the recommended daily allowance (RDA) by the U.S. Food and Drug Administration (FDA) is 60 mg of vitamin C. In this invention, the effective dose of vitamin C administered is at least about 200 mg. This is more than triple the current RDA for vitamin C. The preferred daily dose of vitamin C in the current invention is in the range of from about 0.5 g to about 1.5 g. Except for vitamins A and E, no RDA has been established for other antioxidants. Excess of vitamin A and E in the human diet is not recommended and these vitamins are excluded from the use in the current invention. Assuming that weight of a person is at least about 50 kg and no more than about 100 kg, the minimum effective daily dose in the current invention for lycopene is about 20 mg, and for gallic acid is about 100 mg. The preferred daily dose for lycopene is in the range of from about 60 mg to about 180 mg, and for gallic acid is in the range of from about 150 mg to about 600 mg.

The amount of phenolic antioxidants can also be expressed as the gallic acid equivalent (GAE), GAE is determined by the Folin-Ciocalteau reaction (Ki, 2003), It has been found that ingestion of relatively high quantities of antioxidants, particularly acidic antioxidants such as ascorbic acid or gallic acid, can result in digestive system problems including excess acidity, heartburn, gastric reflux, nausea, gas or bloating. Supplementing the antioxidant intake with ginger (e.g., ginger root powder), an extract of ginger, rutin or a mixture of those materials, can alleviate these problems. These materials may be administered along with the antioxidants in an amount effective to address the problem, for example, from about 0.1 to about 50 mg/kg per day, preferably from about 1 to about 10 mg/kg per day. The materials may be formulated in a single dosage with the antioxidant, for example, in a dose from about 0.5 to about 500 mg for ginger, and in a dose from about 0.5 to about 50 mg for ginger extract and rutin.

An additional unexpected effect of the topical compositions of the current invention is their moisturizing effect on the skin. This effect benefits skin texture and reduces the appearance of wrinkles in aging skin, In the method of treatment aspect of the present invention, the antioxidant-containing supplement is administered orally, concurrently with a topical treatment to improve the skin condition.

By "concurrent treatment" is meant that the oral supplement is administered in its recommended dosage over the same time period that the topical treatment is administered in its recommended dosage. For example, during a given two-week period, the oral lycopene (or antioxidant) supplement is administered once per day and the topical ointment is applied to a selected area of skin twice a day (for example, morning and before bed).

Any conventional topical treatment to improve skin conditions arising from acne, rosacea, skin inflammation (e.g., topical steroids), irritation and aging (e.g., alpha-hydroxy fatty acids) can be used concurrently with the oral treatment regimen of the present invention.

A preferred treatment utilizes the topical application of an active material having the following formula:

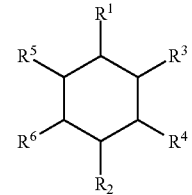

In this formula, $R^1$ is selected from —OH and $C_1$-$C_3$ alkyl OH ($C_1$-$C_3$ alkanols); and $R^2$, $R^3$, $R^4$, $R^5$ and $R^6$ are independently selected from —H, —OH, —COOH, $C_1$-$C_6$ alkyl and $C_3$-$C_6$ cycloalkyl. The total number of —OH groups in the active material should not exceed five. In this formula it is preferred that $R^2$, $R^3$, $R^4$, $R^5$ and $R^6$ be selected from —H and —OH, and further that the molecule in its entirety contains no more than five hydroxyl groups, and preferably no more than three hydroxyl groups. Preferred compounds for use in the present invention are selected from cyclohexanol, 2-cyclohexylethanol, cyclohexylmethanol, 3-cyclohexyl-1-propanol, 1,4-cyclohexanediol, 1,3-cyclohexanediol, 1,2-cyclohexanediol, 4-cyclohexylcyclo-hexanol, 4-methylcyclohexanol, 1,2,3-cyclohexanetriol, 1,3,5-cyclohexanetriol, and 1.4.5-cyclohexanetriol. Mixtures of these materials may also be used. Both the cis and trans isomers (or mixtures) of the active materials can be used herein. Stereochemical isomers and phospho- and phosphatidylo-derivatives, and metabolites of the active compounds are intended to be included within these compound definitions.

Particularly preferred compounds for use in the topical treatment aspect of the present invention include 1,2-cyclohexanediol, 1,3-cyclohexanediol, 1,4-cyclohexanediol, 1,3,5-cyclohexanetriol and 1,2,3-cyclohexanetriol, and mixtures of those materials. The cis and trans isomers, as well as the various optical isomers of these materials, are active in the present invention as well.

The active material is applied topically to the skin at the site to be treated (e.g., the site where there is skin redness or symptoms associated with, for example, rosacea, acne or skin inflammation). The active material is typically applied to the skin in an amount of from about 0.001 to about 10 mg/cm$^2$, preferably from about 0.1 to about 1 mg/cm$^2$, more preferably from about 0.1 to about 0.5 mg/cm$^2$, but this can vary depending upon the formulation, the person treated and the nature of the specific condition being treated. Maintaining healthy looking skin and relieving skin conditions, in the context of the present invention, includes maintaining healthy scalp and hair; soothing irritated skin; reducing redness, swelling and skin scars; maintaining skin texture; unplugging clogged and inflamed pores; and improving skin conditions and alleviating skin problems comprising reduction or elimination of symptoms related to skin spots, blemishes and inflammation, and improvement in appearance of aged skin. The active material may be applied in combination with a pharmaceutical or cosmetic additives and topical carriers. Topical pharmaceutical or cosmetic additives and carriers are well known in the art and are described, for example, in U.S. Pat. No. 6,723,755, Chomczynski, issued Apr. 20, 2004; U.S. Pat. No. 6,696,069, Harichian et al., issued Feb. 24, 2004; U.S. Pat. No. 6,692,754, Makimoto et al., issued Feb. 17, 2004; U.S. Pat. No. 6,660,283, Breton et al., issued Dec. 9, 2003; and U.S. Pat. No. 6,623,778, Harichian et al., issued Sep. 23, 2003; all of which are incorporated herein by reference.

When used with a topical carrier, the active material and the topical carrier together comprise a topical composition. In such topical compositions, the active material generally comprises from about 0.001% to about 10% of the composition, with the balance comprising the carrier.

EXAMPLES

The following oral supplements are used alone or in conjunction with the topical compositions containing cyclohexanol derivatives. The topical composition is applied twice a day in the morning and evening hours to an area of skin redness. The topical composition comprises 0.5% Carbomer 940 (Spectrum Quality Products, Gardena, Calif.), 1% 1,4-cyclohexanediol (cis/trans), 0.3% glycerin and water (balance to 100%). The solution is adjusted with sodium hydroxide to pH 7.0.

When oral and topical treatments are administered concurrently, the oral supplements are consumed once a day or two times a day in the morning and evening in the amount indicated below. In each example, after two weeks, the skin redness is reduced or eliminated.

Example 1

Tomato Juice Supplement

Tomato juice (Tomato Drink, Cinna Health Products, Molecular Research Center, Inc., Cincinnati, Ohio) containing 300 mg vitamin C/liter and supplemented with 20 mg pantothenol/liter. 250 ml of juice is consumed once a day.

Example 2

Tomato Paste Supplement 200 g of tomato paste (HUNT'S® tomato paste, ConAgra Dietaries, Irvine, Calif.) containing 36 mg vitamin C and 300 IU vitamin A is mixed with 1000 ml of water. 250 ml of the mixture is consumed once a day.

Example 3

Lycopene Pill Supplement

Lycopene pills (Nature's Bounty, Inc., Bohemia, N.Y.), each containing 5 mg lycopene dissolved in soybean oil, are administered orally (5 pills consumed once a day).

Example 4

Water-Extracted Supplement 340 g of tomato paste (HUNT'S® tomato paste) is mixed with 660 ml water and the mixture is stored at room temperature. After 6 hours of storage, the mixture is sedimented and a lycopene-containing pellet is again extracted with 660 ml water. The resulting water-extracted pellet is suspended in 660 ml of water. 200 ml of the suspension is consumed once a day.

Example 5

Acidic Water-Extracted Supplement 340 g of tomato paste (HUNT'S® tomato paste) is mixed with 660 ml water. The mixture is acidified to pH 3 with HCl and stored at room temperature. After 6 hours of storage, the mixture is sedimented and a lycopene containing pellet is again extracted with 660 ml water at pH 3. The resulting acid-extracted pellet is suspended in 660 ml of water. The pH of the mixture is adjusted to pH 4 with sodium hydroxide. 200 ml of the suspension is mixed with 0.5 ml of corn oil (ACH Dietary Companies, Inc., Memphis, Tenn.) and consumed once a day.

Example 6

Acid-Extracted Tomato Supplement Mixed With Grapefruit Juice 340 g of tomato paste (HUNT'S® tomato paste) is mixed with 660 ml water. The mixture is acidified to pH 3 with HCl and stored at room temperature. After 6 hours of storage, the mixture is sedimented and a lycopene-containing pellet is again extracted with 660 ml water at pH 3, The resulting acid-extracted pellet is suspended in 660 ml of Ruby Red grapefruit juice (Citrus World, Inc.: Lake Wales, Fla.) containing 300 mg/liter vitamin C and 0.4 mg thiamine/liter. The pH of the mixture is adjusted to pH 4 with sodium hydroxide. 200 ml of the suspension is consumed once a day.

Example 7

Acid-Extracted Tomato Supplement Mixed With Apple Puree 340 g of tomato paste (HUNT'S® tomato paste) is mixed with 660 ml water. The mixture is acidified to pH 3 with HCl and stored at room temperature. After 6 hours of storage, the mixture is sedimented and a lycopene-containing pellet is again extracted with 660 ml water at pH 3. The resulting acid-extracted pellet is mixed with 450 g of apple sauce (Mott's Inc., Stamford, Conn.) containing 48 mg vitamin C. The pH of the mixture is adjusted to pH 4 with sodium hydroxide. 90 g of the mixture is consumed once a day.

Example 8

Acid-Extracted Tomato/Apple Supplement Fortified With Vitamins 340 g of tomato paste (HUNT'S® tomato paste) is mixed with 660 ml water. After 6 hours of storage, the mixture is sedimented and a lycopene-containing pellet is again extracted with 660 ml water at pH 3, The resulting acid-extracted pellet is suspended in 450 g of apple puree. The pH of the mixture is adjusted to pH 4 with sodium hydroxide. 90 g of the mixture is mixed with a crushed multivitamin pill (CENTRUM®, Wyeth Consumer Healthcare, Madison, N.J.) and consumed once a day. The multivitamin pill contains vitamin A 3500 IU, vitamin C 60 mg, vitamin D 400 IU, vitamin E 45 IU, vitamin K 0.01 mg, thiamin 1.5 mg, riboflavin 1.7 mg, niacin 20 mg, vitamin B6 3 mg, folic acid 0.4 mg, vitamin B 12 0.025 mg, biotin 0.03 mg, pantothenic acid 10 mg, calcium 0.2 g, phosphorus 48 mg, iodine 0.15 mg, magnesium 0.1 g, zinc 15 mg, selenium 0.02 mg, copper 2 mg, chromium 0.15 mg, molybdenum 0.075 mg, chloride 0.075 mg, potassium 80 mg, boron 0.015 mg, nickel 0.005 mg, silicon 2 mg, vanadium 0.01 mg, lutein 0.25 mg and lycopene 0.3 mg.

Example 9

Tomato Juice With Gallic Acid Supplement 1 l of Tomato Drink (Cinna Health Products, MRC, Inc., Cincinnati, Ohio) containing tomato paste, corn oil, salt and ascorbic acid (400 mg/l) is supplemented with 800 mg of gallic acid and 200 mg rutin (Spectrum Quality Products, Inc.), pH=4.7. 200 ml of the Drink is consumed once a day.

Example 10

Pineapple Juice With Gallic Acid Supplement 1 l of pineapple juice (Dole Packaged Foods Corp., Westlake Village, Calif.) containing 678 mg of vitamin C is supplemented with 1 g of gallic acid (Spectrum Quality Products, Inc.), 200 mg of the juice is consumed twice a day, Example 11

Gallic Acid Pill 200 mg of gallic acid (Spectrum Quality Products, Inc.) is enclosed in a vegetable capsule (Capsuline, Fla.). Two pills are consumed daily before breakfast and dinner.

Example 12

Vitamin C Pill 1 g of ascorbic acid (Spectrum Quality Products, Inc.) is enclosed in a vegetable capsule (Capsuline, Fla.). Two pills are consumed daily before breakfast and dinner.

These lycopene and antioxidant supplements may be taken concurrently with a topical skin treatment, such as cyclohexanediol, to improve acne, rosacea, skin inflammation or irritation in a patient, Further, the supplements defined above may contain from about 50 mg to about 250 mg dried ginger root powder to alleviate stomach discomfort that may accompany ingestion of high levels of antioxidants,

REFERENCES

Deming, D. M. and Erdman, J. W., Mammalian Carotenoid Absorption and Metabolism, Pure Appl Chem, 71, 2213-2223.

Felter H. W., Lloyd J. U. Acidum Gallicum-Gallic Acid in King's American Dispensatory.

Friedman, M. and Jurgens, H. S., Effect of pH on the Stability of Plant Phenolic Compounds, J Agri Chem, 2000, 2101-2110.

Hof, K. H. et al., Carotenoid Bioavailability in Humans from Tomatoes Processed in Different Ways Determined from the Carotenoid Response in the Triglyceride-Rich Lipoprotein Fraction of Plasma after Single Consumption and in Plasma after Four Days of Consumption, J. Nutr, 2000, 130, 1189-1196.

Khachik, F. et al., Chemistry, Distribution, and Metabolism of Tomato Carotenoids and Their Impact on Human Health, Exp Biol Med 2002, 227, 845-851.

Ki et al., Cocoa Has More Phenolic Phytochemicals and a Higher Antioxidant Capacity than Teas and Red Wine, J. Agric. Food Chem., 51(25):7292-7295 (2003).

Ow, Y. Y., Stupans, J., Gallic Acid and Gallic Acid Derivatives: Effect on Drug Metabolizing Enzymes, Curr. Drug Metab., 2003, 4, 241-248.

Shahrzad S., Aoyagi K., Winter A., Koyama A. and Bitsch I, Pharmacokinetics of Gallic Acid and Its relative Bioavailbility from Tea in Healthy Humans, J. Nutr. 2001, 131, 1207-1210.

Tyssandier, V. et al., Processing of Vegetable-Borne Carotenoids in the Human Stomach and Duodenum, A. J. Pyhysiol Gastroinest Liver Physiol, 284, G913-G923.

H. J. Heinz Company, sponsor, www.lycopene.org.

National Rosacea Society, www.rosacea.org.

What is claimed is:

1. A stabilized lycopene-containing oral composition comprising:
    (a) an effective amount of a solid fraction obtained from a tomato extraction process, wherein said extraction process consists essentially of extracting tomato material in acidified water which has been acidified with one or more acids to a pH from 1.5 to 6, at a temperature of from about 15° C. to about 25° C. under atmospheric pressure and wherein the solids are substantially free of tomato taste and odor; and
    (b) a pharmaceutical and/or food-grade carrier.

2. A composition according to claim 1 further comprising non-lycopene plant material.

3. A composition according to claim 1 further comprising adjunct materials selected from vitamins, antioxidants, microelements, natural extracts, dietary additives, hormones, proteins, fatty acids, oils, alcohols, carbohydrates, and mixtures thereof.

4. A composition according to claim 1 wherein the acid added to the solvent is hydrochloric acid.

5. A composition according to claim 2 wherein the non-lycopene plant material is selected from juices, extracts or purees, derived from sources selected from apples, bananas, pears, grapes, cocoa, and herbs.

* * * * *